US008586942B2

United States Patent
Honda et al.

(10) Patent No.: US 8,586,942 B2
(45) Date of Patent: Nov. 19, 2013

(54) BEAM POSITION MONITOR AND PARTICLE BEAM THERAPY SYSTEM

(75) Inventors: Taizo Honda, Chiyoda-ku (JP); Hisashi Harada, Chiyoda-ku (JP); Yuehu Pu, Chiyoda-ku (JP); Masahiro Ikeda, Chiyoda-ku (JP); Kazushi Hanakawa, Chiyoda-ku (JP); Toshihiro Otani, Chiyoda-ku (JP); Tadashi Katayose, Chiyoda-ku (JP); Yukiko Yamada, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/639,998

(22) PCT Filed: Jan. 20, 2012

(86) PCT No.: PCT/JP2012/051195
§ 371 (c)(1),
(2), (4) Date: Oct. 8, 2012

(87) PCT Pub. No.: WO2013/108393
PCT Pub. Date: Jul. 25, 2013

(65) Prior Publication Data
US 2013/0190548 A1    Jul. 25, 2013

(51) Int. Cl.
H01J 3/10    (2006.01)
(52) U.S. Cl.
USPC ............. 250/397; 250/492.1; 250/492.2; 250/492.3
(58) Field of Classification Search
USPC ............... 250/397, 492.1–492.3
See application file for complete search history.

(56) References Cited

U.S. PATENT DOCUMENTS

2008/0061245 A1    3/2008    Yamamoto

FOREIGN PATENT DOCUMENTS

| JP | 3-103795 A | 4/1991 |
| JP | 2002-006051 A | 1/2002 |
| JP | 2002-280199 A | 9/2002 |
| JP | 2003-297600 A | 10/2003 |
| JP | 2008-064664 A | 3/2008 |
| JP | 2009-050468 A | 3/2009 |
| JP | 2010-060523 A | 3/2010 |

OTHER PUBLICATIONS

International Search Report (PCT/ISA/210) issued on Mar. 6, 2012, by the Japanese Patent Office as the International Searching Authority for International Application No. PCT/JP2012/051195.

*Primary Examiner* — Michael Maskell
(74) *Attorney, Agent, or Firm* — Buchanan Ingersoll & Rooney PC

(57) ABSTRACT

A charged particle beam position monitor is provided with a plurality of position monitors and a beam data processing device that performs calculation processing of the state of a charged particle beam, based on a plurality of signals outputted from the position monitors. The beam data processing device includes a plurality of channel data conversion units that perform AD conversion processing of the plurality of signals outputted from the position monitors; a position size processing unit, for each of the position monitors, that calculates the beam position of the beam, based on voltage information obtained through the AD conversion processing; and an integrated control unit that controls the plurality of channel data conversion units in such a way that while the beam is irradiated onto an irradiation subject, AD conversion processing of the signals is performed at different timings for the respective position monitors.

18 Claims, 6 Drawing Sheets

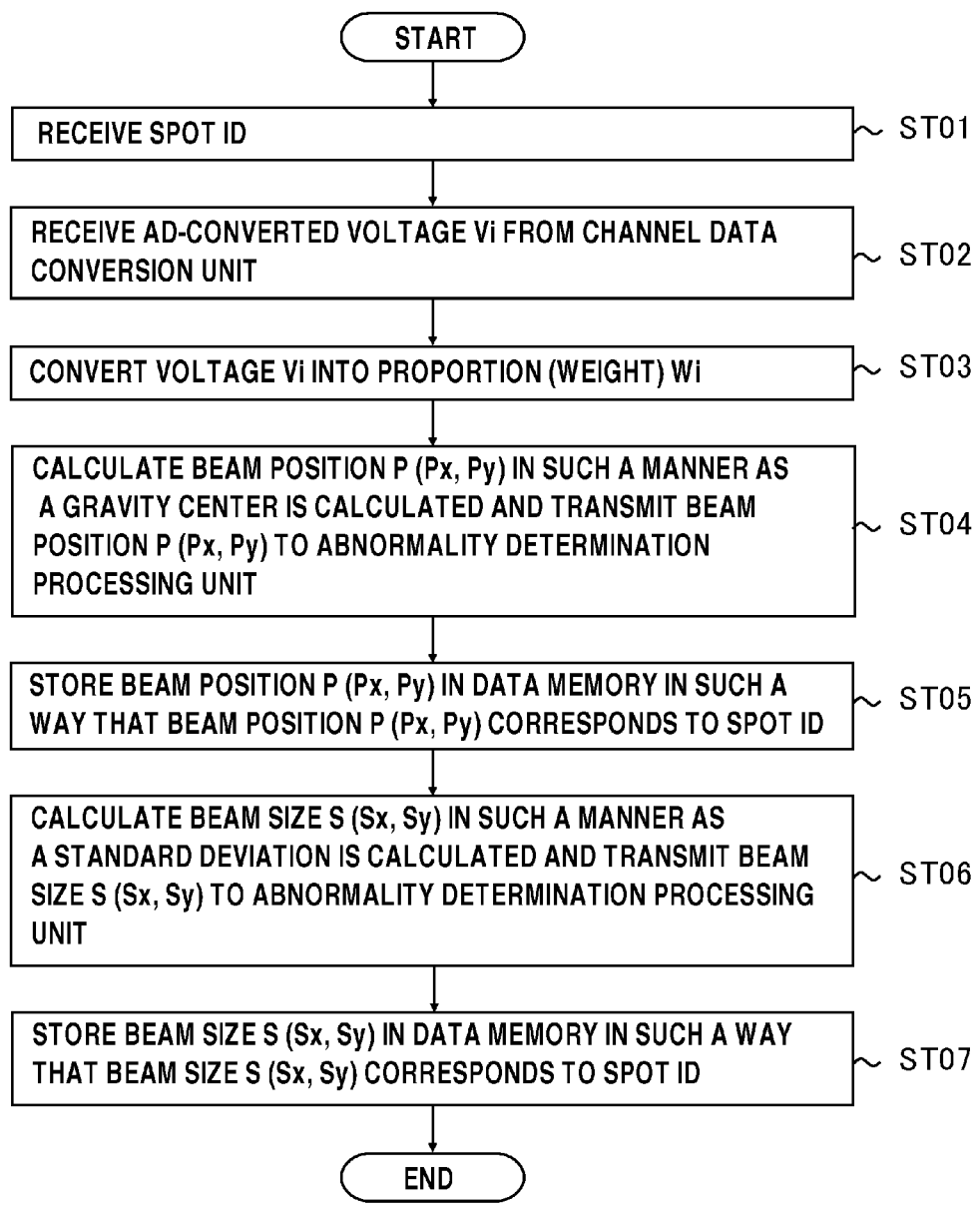

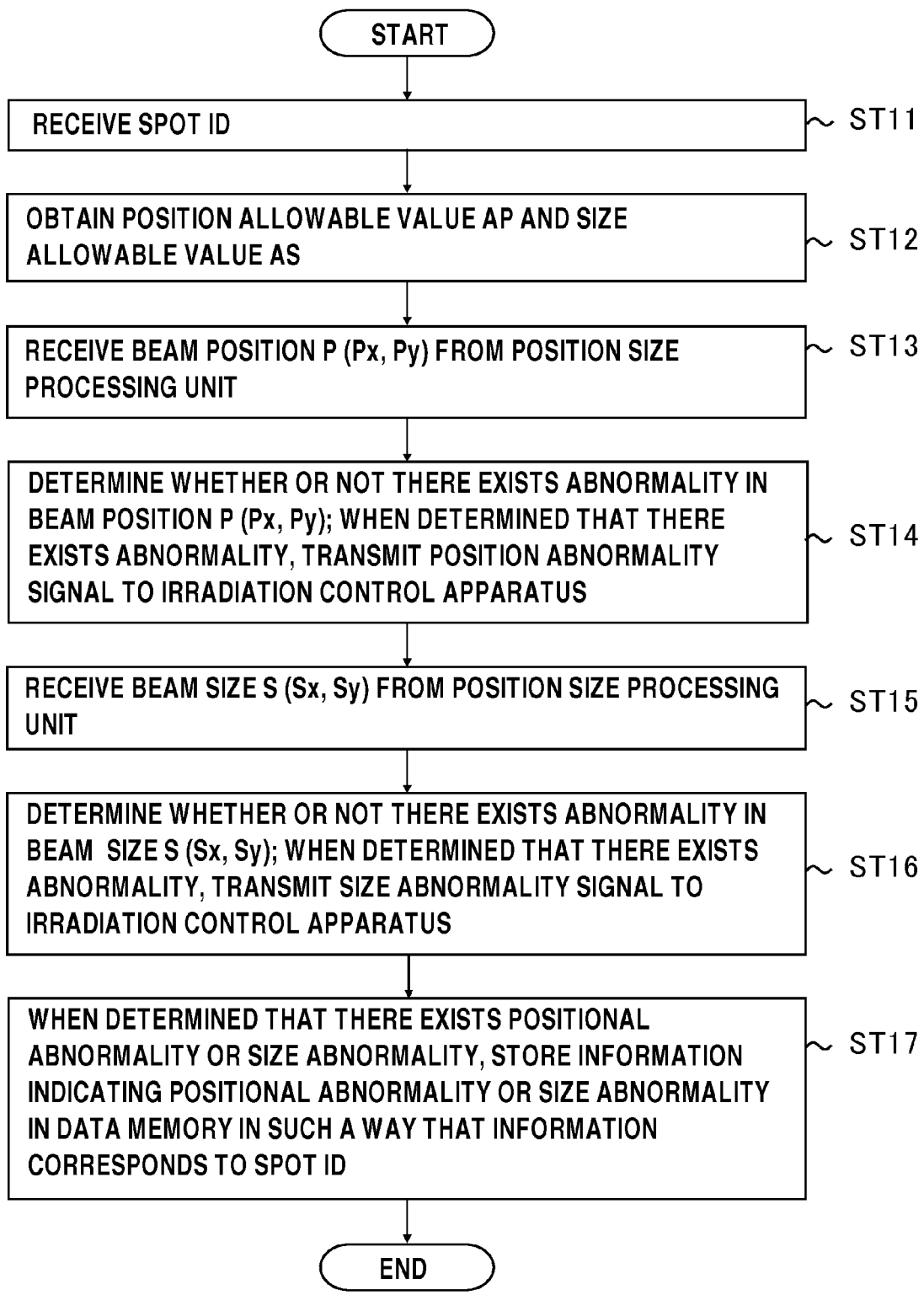

BEAM POSITION MONITOR AND PARTICLE BEAM THERAPY SYSTEM

TECHNICAL FIELD

The present invention relates to a particle beam therapy system utilized in the medical field and R&Ds and particularly to data processing of the position and the size of a particle beam in a particle beam therapy system of a scanning type such as a spot-scanning type or a raster-scanning type.

BACKGROUND ART

In general, a particle beam therapy system is provided with a beam generation apparatus that generates a charged particle beam, an accelerator that is connected with the beam generation apparatus and accelerates a generated charged particle beam, a beam transport system that transports a charged particle beam that is accelerated by the accelerator so as to gain predetermined energy and then emitted, and a particle beam irradiation apparatus, disposed at the downstream side of the beam transport system, for irradiating a charged particle beam onto an irradiation subject. Particle beam irradiation apparatuses are roughly divided into apparatuses utilizing a broad irradiation method in which a charged particle beam is enlarged in a dispersion manner by a scatterer, and the shape of the enlarged charged particle beam is made to coincide with the shape of an irradiation subject in order to form an irradiation field; and apparatuses utilizing a scanning irradiation method (the spot-scanning method, the raster-scanning method, and the like) in which an irradiation field is formed by performing scanning with a thin, pencil-like beam in such a way that the scanning area coincides with the shape of an irradiation subject.

In the broad irradiation method, an irradiation field that coincides with the shape of a diseased site is formed by use of a collimator or a bolus. The broad irradiation method is a most universally utilized and superior irradiation method where an irradiation field that coincides with the shape of a diseased site is formed so as to prevent unnecessary irradiation onto a normal tissue. However, it is required to create a bolus for each patient or to change the shape of a collimator in accordance with a diseased site.

In contrast, the scanning irradiation method is a high-flexibility irradiation method where, for example, neither collimator nor bolus is required. However, because these components for preventing irradiation onto not a diseased site but a normal tissue are not utilized, there is required a positional accuracy of beam irradiation that is the same as or higher than that of the broad irradiation method.

Patent Document 1 discloses a beam position monitor, for a particle beam therapy system, that has a purpose of solving the problem that in a raster-scanning irradiation method in which when the irradiation position is changed, the charged particle beam is kept to irradiate, the accuracy of beam position measurement is deteriorated mainly by the fact that the electric charges collected during the scanning of the charged particle beam and the electric charges collected when the scanning has been completed cannot accurately be distinguished from each other. The beam position monitor according to Patent Document 1 is provided with a collection electrode (corresponding to a sensor unit of the position monitor) for collecting collection charges produced by ionization of the charged particle beam, and a signal processing circuit that performs a beam position calculation for determining the beam position by utilizing collection charges. The signal processing circuit is provided with an I/V converter that generates a voltage signal obtained by I/V-converting the current output from the collection electrode; a digital signal generation circuit that generates a digital signal related to the collection charges when the voltage signal is inputted thereto; a timing signal transmission/reception unit that receives a signal, as a timing signal, that is generated at a time when the charged particle beam, which is scanned from a scanning-stop irradiation point (corresponding to an irradiation spot in a spot scanning irradiation method) to the next scanning-stop irradiation point, is in the non-scanning state (in which the charged particle beam is stopped at the scanning-stop irradiation point); and a beam position calculation unit that calculates a beam position by use of a digital signal related to collection charges when a digital signal, related to the collection charges, generated by the digital signal generation circuit at the timing when the timing signal transmission/reception unit receives the timing signal, is inputted thereto.

PRIOR ART REFERENCE

Patent Document

[Patent Document 1] Japanese Patent Application Laid-Open No. 2010-60523 (Paragraphs 0008 through 0011, FIG. 1)

DISCLOSURE OF THE INVENTION

Problems to be Solved by the Invention

In a particle beam therapy system according to a scanning irradiation method, high accuracy of beam irradiation position is required; therefore, it is required to frequently ascertain the beam position by use of a beam position monitor. The beam position monitor is provided with, for example, a position monitor that detects the passing position of a charged particle beam through a plurality of detection channels; and a beam data processing device that calculates a beam position, which is the passing position of a charged particle beam at the position monitor, based on a plurality of analogue signals outputted from the position monitor. The beam data processing device is disposed in the vicinity of the position monitor. It is required to prevent an electronic device that forms the beam data processing device from erroneously operating due to the effect of radiations emitted when a charged particle beam is irradiated; therefore, it is restricted to separately raise the operation speed thereof.

In the invention disclosed in Patent document 1, irradiation position data at a time when the scanning of a charged particle beam is stopped at a scanning-stop irradiation point set on a treatment subject and then the charged particle beam is irradiated can be obtained only once at the timing of a signal to be generated in the non-scanning state where no charged particle beam is scanned; however, this is made possible only when the irradiation position data obtaining cycle is longer than the irradiation position data processing time. As described above, the beam position monitor according to Patent Document 1 undergoes the effect of radiations emitted when a charged particle beam is irradiated; therefore, because it is required to prevent the beam position monitor from erroneously operating due to the effect of the radiations, the operation speed of the electronic device cannot separately be raised, whereby the irradiation position data obtaining cycle cannot be shortened.

In the case where the irradiation position data obtaining cycle is shorter than the irradiation position data processing time, there has been a problem that because provided with no appropriate contrivance, the beam position monitor cannot continue obtaining the irradiation position data at the scanning-stop irradiation point. Accordingly, in the case where beam position data is definitely obtained at each scanning-stop irradiation point, the particle beam therapy needs to be implemented according to an irradiation method based on a scanning pattern in which it is made possible to continue obtaining the irradiation position data at scanning-stop Irradiation points; therefore, it is possible neither to implement high-accuracy charged particle beam irradiation in which the safety is raised by obtaining a plurality of data items at a single and the same scanning-stop irradiation point nor to shorten the one-time therapy time in a particle beam therapy by shortening the irradiation time at a scanning-stop irradiation point.

The present invention has been implemented in order to solve the foregoing problems; the objective thereof is to shorten the obtaining cycle for a charged particle beam irradiation position even in the case where radiations, emitted when a charged particle beam is irradiated, provide an effect.

Means for Solving the Problems

The beam position monitor according to the present invention is provided with a plurality of position monitors that detect a passing position of the charged particle beam through a plurality of detection channels; and a beam data processing device that performs calculation processing of the state of the charged particle beam, based on a plurality of analogue signals outputted from the plurality of position monitors. The beam data processing device includes a plurality of channel data conversion units, a plurality of position size processing units that process each of the plurality of position monitors, and an integrated control unit. The plurality of channel data conversion units perform AD conversion processing in which each of the plurality of analogue signals outputted from the position monitors is converted into a digital signal. The position size processing unit calculates a beam position, which is the passing position of a charged particle beam in the position monitor, based on a plurality of voltage information items obtained through processing by the plurality of channel data conversion units. The integrated control unit controls the plurality of channel data conversion units in such a way that while the charges particle beam is irradiated onto an irradiation subject, the AD conversion processing is performed at different timings for the respective position monitors.

Advantage of the Invention

In a beam position monitor according to the present invention, the integrated control unit controls the plurality of channel data conversion units in such a way that the plurality of analogue signals are AD-converted at different timings for the respective corresponding position monitors; therefore, the irradiation position of a charged particle beam can be obtained in a short obtaining cycle even in the case where radiations, emitted when the charged particle beam is irradiated, provide an effect.

BRIEF DESCRIPTION OF THE DRAWINGS

FIG. 5 is a flowchart for explaining the operation of a position size processing unit in FIG. 1; and FIG. 6 is a flowchart for explaining the operation of an abnormality determination processing unit in FIG. 1.

BEST MODE FOR CARRYING OUT THE INVENTION

Embodiment 1

Figure 1:
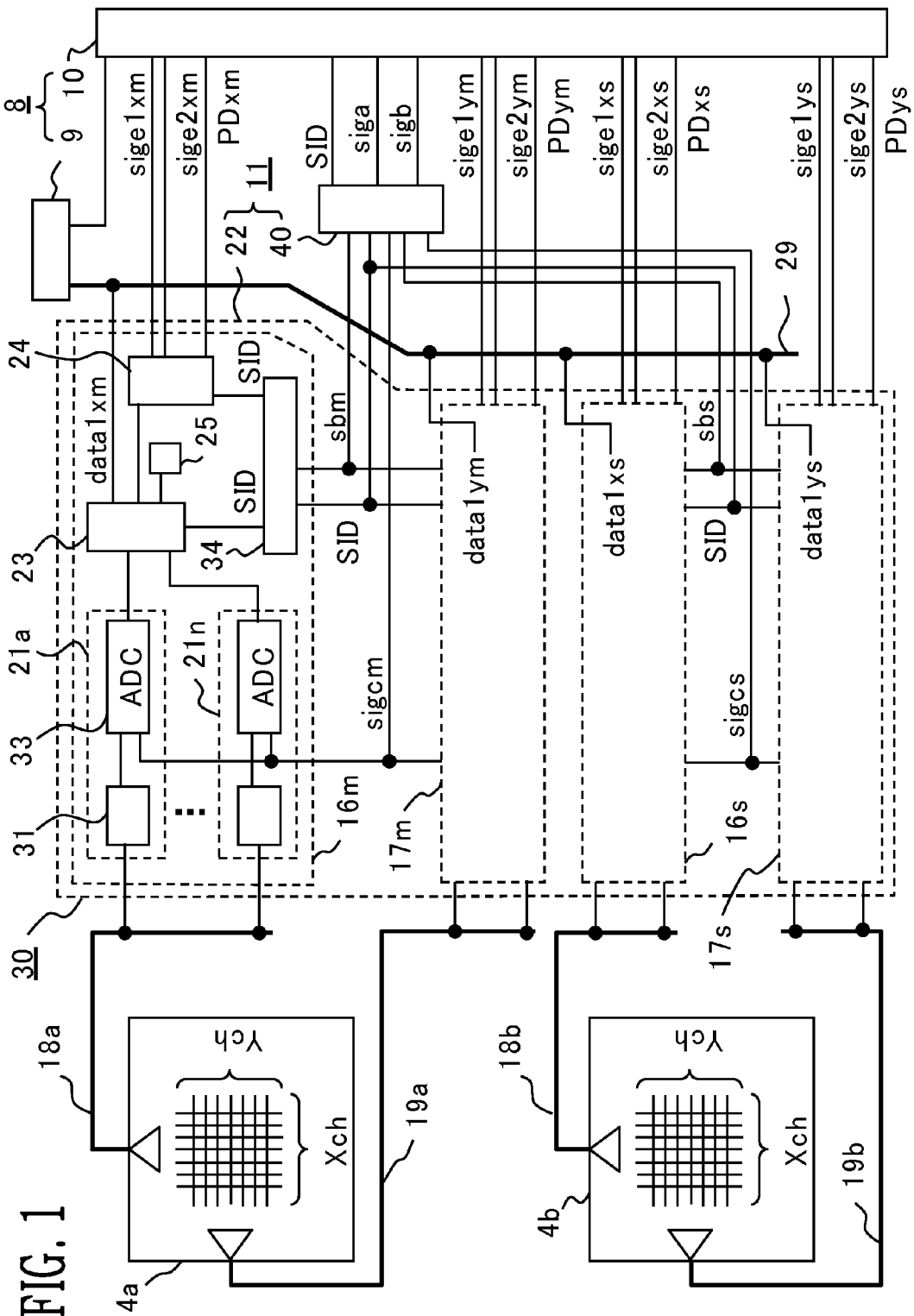
FIG. 1 is a diagram illustrating the configuration of a beam position monitor according to Embodiment 1 of the present invention.
Figure 2:
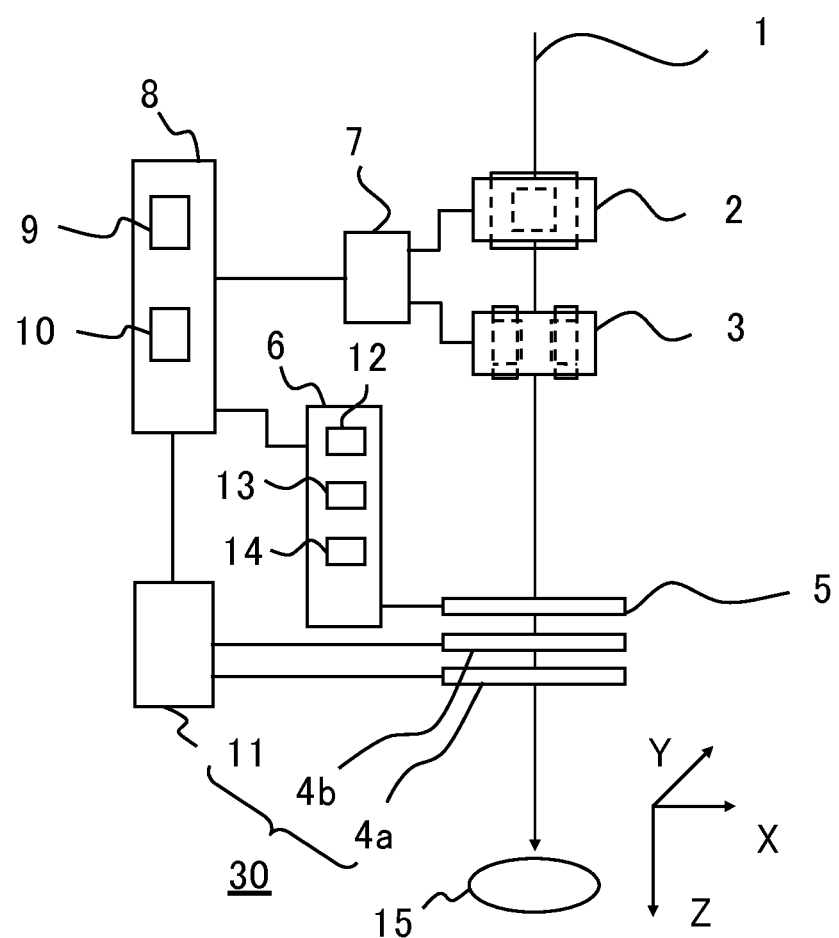
FIG. 2 is a diagram illustrating the configuration of a particle beam irradiation apparatus provided with the beam position monitor in FIG. 1.
Figure 3:
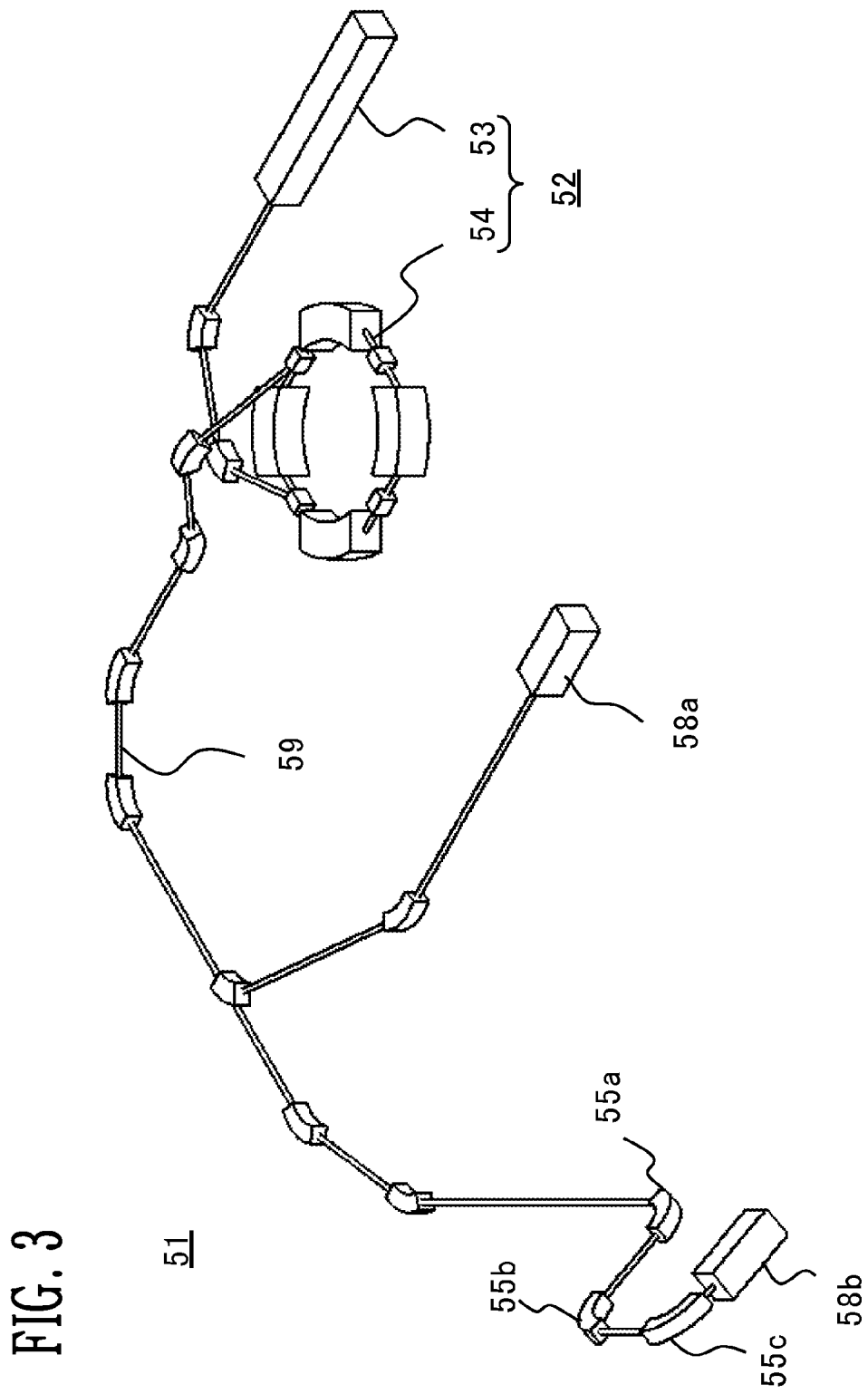
FIG. 3 is a schematic configuration diagram illustrating a particle beam therapy system according to Embodiment 1 of the present invention.

FIG. 1 is a diagram illustrating the configuration of a beam position monitor according to Embodiment 1 of the present invention. FIG. 2 is a diagram illustrating the configuration of a particle beam irradiation apparatus provided with a beam position monitor according to Embodiment 1 of the present invention; FIG. 3 is a schematic configuration diagram illustrating a particle beam therapy system according to Embodiment 1 of the present invention. In FIG. 3, a particle beam therapy system 51 includes a beam generation apparatus 52, a beam transport system 59, and particle beam irradiation apparatuses 58a and 58b. The beam generation apparatus 52 includes an ion source (unillustrated), a prestage accelerator 53, and a synchrotron 54. The particle beam irradiation apparatus 58b is provided in a rotating gantry (unillustrated). The particle beam irradiation apparatus 58a is provided in a treatment room where no rotating gantry is installed. The function of the beam transport system 59 is to achieve communication between the synchrotron 54 and the particle beam irradiation apparatuses 58a and 58b. Part of the beam transport system 59 is provided in the rotating gantry (unillustrated), and that part includes a plurality of deflection electromagnets 55a, 55b, and 55c.

A charged particle beam, which is a particle beam such as a proton beam generated in the ion source, is accelerated by the prestage accelerator 53 and enters the synchrotron 54, which is an accelerator. The particle beam is accelerated to gain predetermined energy. The charged particle beam launched from the synchrotron 54 is transported to the particle beam irradiation apparatuses 58a and 58b by way of the beam transport system 59. The particle beam irradiation apparatuses 58a and 58b each irradiate the charged particle beam onto an irradiation subject 15 (refer to FIG. 2). With regard to the particle beam irradiation apparatuses 58a and 58b, common explanations will be made as those for a particle beam irradiation apparatus 58, without utilizing different reference characters.

A charged particle beam 1 generated in the beam generation apparatus 52 and accelerated to gain predetermined energy is led to the particle beam irradiation apparatus 58 by way of the beam transport system 59. In FIG. 2, the particle beam irradiation apparatus 58 is provided with X-direction and Y-direction scanning electromagnets 2 and 3 that scan the charged particle beam 1 in the X direction and the Y direction, respectively, which are directions perpendicular to the charged particle beam 1; position monitors 4a and 4b; a dose monitor 5; a dose data converter 6; a beam data processing device 11; a scanning electromagnet power source 7; and an irradiation management apparatus 8 that controls the particle beam irradiation apparatus 58. The irradiation management apparatus 8 is provided with an irradiation control computer 9 and an irradiation control apparatus 10. The dose data converter 6 is provided with a trigger generation unit 12, a spot counter 13, and an inter-spot counter 14. The position monitor 4a, the position monitor 4b, and the beam data processing device 11 configure a beam position monitor 30. The traveling direction of the charged particle beam 1 is the Z direction. With regard to the position monitors 4a and 4b, common explanations will be made as those for a position monitor 4, without utilizing different reference characters.

The X-direction scanning electromagnet 2 scans the charged particle beam 1 in the X direction, and the Y-direction scanning electromagnet 3 scans the charged particle beam 1 in the Y direction. The position monitors 4a and 4b detect the size and the passing position (gravity center position), of the beam, through which the charged particle beam 1 that has been scanned by the X-direction scanning electromagnet 2 and the Y-direction scanning electromagnet 3 passes. The position monitors 4a and 4b will be referred to as a primary position monitor and a secondary position monitor, respectively, as may be necessary. The dose monitor 5 detects the dose of the charged particle beam 1. The irradiation management apparatus 8 controls the irradiation position of the charged particle beam 1 on the irradiation subject 15, based on treatment plan data created by an unillustrated treatment planning apparatus; when the dose measured by the dose monitor 5 and converted into digital data by the dose data converter 6 reaches the desired dose, the charged particle beam 1 is stopped irradiating. The scanning electromagnet power source 7 changes setting currents for the X-direction scanning electromagnet 2 and the Y-direction scanning electromagnet 3, based on control inputs (commands), which are outputted from the irradiation management apparatus 8, to the X-direction scanning electromagnet 2 and the Y-direction scanning electromagnet 3.

In this Description, the scanning irradiation method of the particle beam irradiation apparatus 58 will be explained assuming that it is a method in which when the irradiation position of the charge particle beam 1 is changed, the charged particle beam 1 is kept to irradiate, and as is the case with a spot-scanning irradiation method, the beam irradiation position travels through spot positions one after another. The spot counter 13 measures the irradiation dose for a time during which the beam irradiation position of the charged particle beam 1 is stopped. The inter-spot counter 14 measures the irradiation dose for a time during which the beam irradiation position of the charged particle beam 1 moves. The trigger generation unit 12 generates a dose completion signal sigb when the dose of the charged particle beam 1 at the beam irradiation position reaches a desired irradiation dose.

In FIG. 1, the beam position monitor 30 includes the position monitor 4a, the position monitor 4b, and the beam data processing device 11. The position monitor 4a and the position monitor 4b are, for example, configured in a single and the same manner. The beam data processing device 11 is provided with a data processing unit 22 and an integrated control unit 40. The data processing unit 22 is provided with a data processing unit of the position monitor 4a, which is a primary position monitor, and a data processing unit of the position monitor 4b, which is a secondary position monitor. The data processing unit of the position monitor 4a includes an X data processing unit 16m that processes the X-channel signal of the position monitor 4a and a Y data processing unit 17m that processes the Y-channel signal of the position monitor 4a. The data processing unit of the position monitor 4b includes an X data processing unit 16s that processes the X-channel signal of the position monitor 4b and a Y data processing unit 17s that processes the Y-channel signal of the position monitor 4b.

The X data processing unit 16m is connected with the position monitor 4a by way of an X-channel signal line 18a; the Y data processing unit 17m is connected with the position monitor 4a by way of a Y-channel signal line 19a. The X data processing unit 16s is connected with the position monitor 4b by way of an X-channel signal line 18b; the Y data processing unit 17s is connected with the position monitor 4b by way of a Y-channel signal line 19b. Each of the X-channel signal lines 18a and 18b and Y-channel signal lines 19a and 19b includes signal lines, the number of which coincides with the number of a plurality of channel data conversion units 21a through 21n. The X data processing units 16m and 16s and the Y data processing units 17m and 17s are configured in a single and the same manner. With regard to the X data processing units 16m and 16s, common explanations will be made as those for an X data processing unit 16, without utilizing different reference characters. Similarly, with regard to the Y data processing units 17m and 17s, common explanations will be made as those for a Y data processing unit 17, without utilizing different reference characters.

The X data processing unit 16m will be explained as an example. The X data processing unit 16m is provided with an ID reception unit 34, a position size processing unit 23, an abnormality determination processing unit 24, a data memory 25, and a plurality of channel data conversion units 21a through 21n, the number of which coincides with the number of a plurality of X-channel signals of the position monitor 4a. In FIG. 1, as far as the channel data conversion units are concerned, only two of them are illustrated; the channel data conversion units between the two channel data conversion units 21a and 21n are omitted by providing a plurality of dots instead of them. Each of the X-channel signal lines 18a and 18b and Y-channel signal lines 19a and 19b is illustrated with a single thick line in FIG. 1, for the purpose of preventing the drawing from becoming complex. The plurality of channel data conversion units 21a through 21n of the X data processing unit 16m and the plurality of channel data conversion units 21a through 21n of the Y data processing unit 17m each configure a data conversion group that is formed corresponding to the primary position monitor 4a. The plurality of channel data conversion units 21a through 21n of the X data processing unit 16s and the plurality of channel data conversion units 21a through 21n of the Y data processing unit 17s each configure a data conversion group that is formed corresponding to the secondary position monitor 4b.

In each of the position monitors 4a and 4b, a sensor unit is provided in the form of a mesh, and a great number of detection channels (channels in the X direction and channels in the Y direction) are provided. These many channels each output a current signal, as an analogue signal. The respective analogue signals of Xch (the X channels) of the position monitor 4a are connected with the channel data conversion units 21a through 21n, of the position monitor 4a, in the X data processing unit 16m; the respective analogue signals of Ych (the Y channels) are connected with the channel data conversion units 21a through 21n, of the position monitor 4a, in the Y data processing unit 17m. Xch corresponds to the X direction of the particle beam irradiation apparatus 58; Ych corresponds to the Y direction of the particle beam irradiation apparatus 58.

The channel data conversion unit 21a is provided with a current/voltage converter 31 that converts a current signal outputted from the position monitor 4a into a voltage signal and a plurality of A/D converters 33 that each perform A/D conversion processing in which the voltage signal obtained through the conversion is converted into a digital signal. The ID reception unit 34 receives ID data, which is identification data for a spot ID (SID), and a strobe signal sbm (sbs) for determining the ID data from the integrated control unit 40, and then transmits the spot ID to the position size processing unit 23 and the abnormality determination processing unit 24. As the reference character for a spot ID, SID is utilized; however, in the case where a spot ID and the reference character SID are expressed in series, the spot ID is expressed as "spot identity SID" in order to prevent confusion between spot ID and reference character SID.

The position size processing unit 23 receives a voltage Vi that has been A/D-converted by the plurality of channel data conversion units 21*a* through 21*n*, and calculates, based on the voltages Vi, a beam position P in such a manner as a gravity center is calculated. The position size processing unit 23 calculates a beam size S based on the voltages Vi, as if a standard deviation is calculated. The beam size S is a length corresponding to 1σ of a one-dimension Gaussian distribution. The position size processing unit 23 of the X data processing unit 16 calculates a beam position Px in the X direction and a beam size Sx in the X direction; the position size processing unit 23 of the Y data processing unit 17 calculates a beam position Py in the Y direction and a beam size Sy in the Y direction. The position size processing unit 23 stores the calculated beam position P and beam size S in the data memory 25. The beam position Px and the beam size Sx are stored in the data memory 25 of the X data processing unit 16; the beam position Py and the beam size Sy are stored in the data memory 25 of the Y data processing unit 17.

Based on preset data PD received from the irradiation control apparatus 10 before the charged particle beam 1 is irradiated, the abnormality determination processing unit 24 determines whether or not there exists an abnormality in the beam position P or in the beam size S, i.e., whether or not the beam position P and the beam size S are allowable. The respective preset data items PDs for the X data processing units 16*m* and 16*s* and the Y data processing units 17*m* and 17*s* are different from one another; the respective preset data items PDs corresponding to the foregoing data processing units, i.e., preset data items PDxm, PDxs, PDym, and PDys are provided. As the reference character of the preset data, "PD" is collectively utilized; however, in the case where the data processing units are separately explained, "PDxm", "PDxs", "PDym", and "PDys" are utilized. This method applies to xm, xs, ym, and ys in other reference characters.

When determining that the beam position P is not allowable, the abnormality determination processing unit 24 outputs a position abnormality signal sige1 to the irradiation control apparatus 10. When determining that the beam size S is not allowable, the abnormality determination processing unit 24 outputs a size abnormality signal sige2 to the irradiation control apparatus 10. The abnormality determination processing unit 24 of the X data processing unit 16*m* outputs a position abnormality signal sige1*xm* and a size abnormality signal sige2*xm*; the abnormality determination processing unit 24 of the Y data processing unit 17*m* outputs a position abnormality signal sige1*ym* and a size abnormality signal sige1*ym*. Similarly, the abnormality determination processing unit 24 of the X data processing unit 16*s* outputs a position abnormality signal sige1*xs* and a size abnormality signal sige1*xs*; the abnormality determination processing unit 24 of the Y data processing unit 17*s* outputs a position abnormality signal sige1*ys* and a size abnormality signal sige2*ys*.

The integrated control unit 40 receives a spot identity SID, which is ID data, an inter-spot travel completion signal siga, and a dose completion signal sigb from the irradiation control apparatus 10 and then transmits signals for performing processing items to the X data processing unit 16*m*, X data processing unit 16*s*, Y data processing unit 17*m*, and Y data processing unit 17*s*. The integrated control unit 40 transmits the spot identity SID to the X data processing units 16*m* and 16*s* and the Y data processing units 17*m* and 17*s*. The integrated control unit 40 transmits an ID strobe sbm for determining the spot identity SID and a processing start signal sigcm for commanding the start of processing to the X data processing unit 16*m* and the Y data processing unit 17*m*. The integrated control unit 40 transmits an ID strobe sbs for determining the spot identity SID and a processing start signal sigcs for commanding the start of processing to the X data processing unit 16*s* and the Y data processing unit 17*s*.

After the irradiation of the charged particle beam 1 has been completed, the respective position size processing units 23 of the X data processing unit 16 and the Y data processing unit each output actual performance data data1 on the beam position P and the beam size S to the irradiation control computer 9 through an actual performance data line 29. As described later, the actual performance data data1 includes information indicating a positional abnormality and a beam size abnormality. The position size processing unit 23 of the X data processing unit 16*m* outputs an actual performance data data1*xm* to the irradiation control computer 9 through the actual performance data line 29; the position size processing unit 23 of the X data processing unit 16*s* outputs an actual performance data data1*xs* to the irradiation control computer 9 through the actual performance data line 29. The position size processing unit 23 of the Y data processing unit 17*m* outputs an actual performance data data1*ym* to the irradiation control computer 9 through the actual performance data line 29; the position size processing unit 23 of the Y data processing unit 17*s* outputs an actual performance data data1*ys* to the irradiation control computer 9 through the actual performance data line 29. In order to prevent the drawing from becoming complex, the actual performance data line 29 is expressed by a single thick line.

The beam data processing device 11 of the beam position monitor 30 alternately processes current signals from the position monitor 4*a* and the position monitor 4*b*, so that even when radiations produced when the charges particle beam 1 is irradiated provides an effect, the obtaining cycle for the irradiation position P and the beam size S of the charged particle beam 1 can be shortened. Because its obtaining cycle for the irradiation position P and the beam size S of the charged particle beam 1 is short, the beam data processing device 11 can twice or more times obtain data on the irradiation position P and the beam size S of the charged particle beam 1 at an irradiation spot. Accordingly, even in the case where when the charged particle beam 1 is being irradiated at an irradiation spot, a positional abnormality or a size abnormality in the charged particle beam 1 is caused, the beam position P, which is the irradiation position of the charged particle beam 1, and the beam size S of the charged particle beam 1 are detected, so that an abnormality detection signal indicating a positional abnormality or a size abnormality in the charged particle beam 1 can be generated. The position abnormality signal sige1 is an abnormality detection signal indicating a positional abnormality in the charged particle beam 1. The position abnormality signal sige2 is an abnormality detection signal indicating a size abnormality in the charged particle beam 1. The operation of the beam position monitor 30 will be explained by use of a timing chart.

Figure 4:
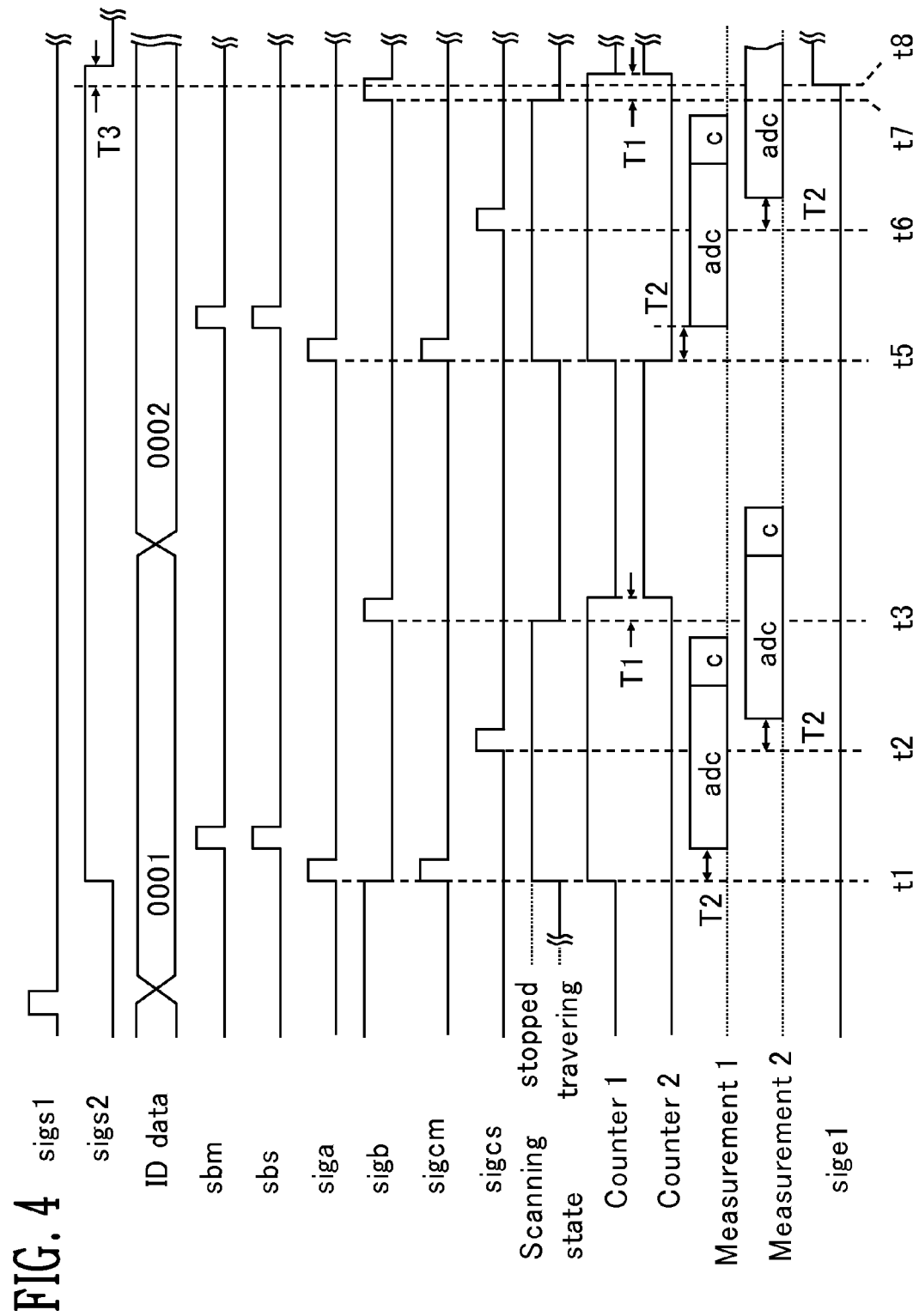
FIG. 4 is a timing chart for explaining the operation of the beam position monitor in FIG. 1.

FIG. 4 is a timing chart for explaining the operation of the beam position monitor. The timing chart in FIG. 4 represents an example in which when the charged particle beam 1 is stopped, data on the charged particle beam 1 is collected twice, i.e., an example in which when the charged particle beam 1 is stopped, data items are collected alternately from the position monitor 4a and the position monitor 4b. In the above example, the processing start signal sigcm for commanding the start of processing of the position monitor 4a and the processing start signal sigcs for commanding the start of processing of the position monitor 4b are pulse signals having a single and the same cycle, and the difference between the rise time of the processing start signal sigcm and the rise time of the processing start signal sigcs is ¼ of the cycle The cycles of the processing start signal sigcm and the processing start signal sigcs and the difference between the rise times thereof are determined in collaboration with the treatment plan.

A timing of Measurement 1 and a timing of Measurement 2 each represent a timing performing AD conversion processing and calculation of the beam position P and the beam size S. A period designated by "adc" indicates the period of AD conversion processing; a period designated by "c" indicates the period of calculation of the beam position P and the beam size S. Trigger signals for starting the A/D conversion processing include the processing start signal sigcm and the processing start signal sigcs. Before the irradiation of the charged particle beam 1 is started, the irradiation control apparatus 10 of the irradiation management apparatus 8 preliminarily transmits all spot identities SIDs to the integrated control unit 40.

The irradiation control apparatus 10 of the irradiation management apparatus 8 transmits a scanning start command sigs1 to the respective apparatuses in the particle beam therapy system 51; then, the irradiation of the charged particle beam 1 is started. After the scanning start command sigs1 is transmitted, the integrated control unit 40 transmits an initial spot identity SID ("0001" in FIG. 4), as ID data, to the ID reception unit 34.

The irradiation control apparatus 10 transmits a beam-on command sigs2 to the beam generation apparatus 52. The charged particle beam 1 is led from the beam generation apparatus 52 to the particle beam irradiation apparatus 58 by way of the beam transport system 59. When receiving from the scanning electromagnet power source 7 a command setting completion signal corresponding to the initial spot identity SID ("0001" in FIG. 4) that has been transmitted to the X-direction scanning electromagnet 2 and the Y-direction scanning electromagnet 3, the irradiation control apparatus 10 transmits to the integrated control unit 40 of the beam position monitor 30 (the time instant t1 in FIG. 4) an inter-spot travel completion signal siga indicating that setting of a command, corresponding to the initial spot identity SID ("0001" in FIG. 4), to the X-direction scanning electromagnet 2 and the Y-direction scanning electromagnet 3 has been completed.

When receiving the inter-spot travel completion signal siga, the integrated control unit 40 transmits the processing start signal sigcm to the channel data conversion units 21a through 21n of the X data processing unit 16m and the channel data conversion units 21a through 21n of the Y data processing unit 17m, transmits the ID strobe sbm to the respective ID reception units 34 of the X data processing unit 16m and the Y data processing unit 17m, and then transmits the ID strove sbs to the respective ID reception units 34 of the X data processing unit 16s and the Y data processing unit 17s (spot initial data collection command procedure).

When receiving the ID strobe sbm or sbs, the ID reception unit 34 takes in ID data at the rise timing thereof. The ID reception unit 34 transmits the taken-in spot identity SID to the position size processing unit 23, and transmits the spot identity to the abnormality determination processing unit 24. In response to the initial ID strobe sbm or sbs in FIG. 4, the ID reception unit 34 takes in the spot identity SID ("0001" in FIG. 4), as ID data. The ID reception unit 34 transmits the taken-in spot identity SID to the position size processing unit 23, and transmits the spot identity to the abnormality determination processing unit 24. When receiving the spot identity SID, the abnormality determination processing unit 24 of the beam data processing device 11 obtains respective data items corresponding to the spot identities SID for the preset data items PDxm, PDym, PDxs, and PDys, which have been preliminarily taken in.

The preset data PD includes a desired position Pd (Pdx, Pdy) and a position allowable value AP for performing abnormality determination on the beam position P (Px, Py) and a desired beam size Sd (Sdx, Sdy) and a size allowable value AS for performing abnormality determination on the beam size S (Sx, Sy). The preset data items PDxm and PDym for the X data processing unit 16m and the Y data processing unit 17m that process data for the primary position monitor 4a include a desired position Pd (Pdxm, Pdym) and a position allowable value APm and a desired beam size Sd (Sdxm, Sdym) and a size allowable value ASm. The preset data items PDxs and PDys for the X data processing unit 16s and the Y data processing unit 17s that process data for the secondary position monitor 4b include a desired position Pd (Pdxs, Pdys) and a position allowable value APs, and a desired beam size Sd (Sdxs, Sdys) and a size allowable value ASs.

As represented in Measurement 1 in FIG. 4, when receiving the processing start signal sigcm from the integrated control unit 40, the A/D converter 33 in each of the X data processing unit 16m and the Y data processing unit 17m starts AD conversion processing at a time when a measurement delay time T2, which is the state transient time in the monitor, has elapsed after the rise of the processing start signal sigcm. As described above, taking a particle that arrives in a delayed manner into consideration, the start of AD conversion processing is delayed (a spot initial data collection procedure).

When a predetermined time (start delay time) equivalent to the difference between the respective rise times of the processing start signal sigcm and the processing start signal sigcs elapses from the time instant t1, i.e., at the time instant t2, the integrated control unit 40 transmits the processing start signal sigcs to the channel data conversion unit 21a through 21n in each of the X data processing unit 16s and the Y data processing unit 17s (a spot intermediate data collection command procedure). As represented in Measurement 2 in FIG. 4, when receiving the processing start signal sigcs from the integrated control unit 40, the A/D converter 33 in each of the X data processing unit 16s and the Y data processing unit 17s starts AD conversion processing at a time when a measurement delay time T2, which is the state transient time in the monitor, has elapsed after the rise of the processing start signal sigcs (a spot intermediate data collection procedure).

After the completion of the A/D conversion processing, the A/D converter 33 in each of the channel data conversion units 21a through 21n transmits the beam data to the position size processing unit 23. Based on the beam data collected in the channel data conversion units 21a through 21n, the position size processing unit 23 calculates the beam position P and the beam size S (a position size calculation procedure).

After receiving the beam position P and the beam size S from the position size processing unit 23, the abnormality determination processing unit 24 determines whether or not the beam position P and the beam size S are allowable, based on the preset data PD. In the case where the beam position P and the beam size S are allowable, the abnormality determination processing unit 24 ends the determination processing. The operation of the abnormality determination processing unit 24 at a time when the beam position P and the beam size S are not allowable will be described later.

When the dose of the charged particle beam 1 is in the state of dose completion reaching the desired irradiation dose at an irradiation spot corresponding to the spot identity SID, the trigger generation unit 12 of the dose data converter 6 transmits a dose completion signal to the irradiation control apparatus 10. When receiving the dose completion signal, the irradiation control apparatus 10 transmits a command corresponding to the next spot identity SID ("0002" in FIG. 4) to the X-direction scanning electromagnet 2 and the Y-direction scanning electromagnet 3 and concurrently outputs the dose completion signal sigh to the integrated control unit 40 (the time instant t3 in FIG. 4).

When a predetermined time has elapses after receiving the dose completion signal sigb, the integrated control unit 40 transmits the spot identity SID ("0002" in FIG. 4), as ID data, to the ID reception unit 34.

Waveforms of the counters 1 and 2 in FIG. 4 represents the counting periods (dose measurement periods) of the spot counter 13 and the inter-spot counter 14, respectively. The upper side (state 1) of each waveform suggests that the counting is being performed, and the lower side (state 0) of each waveform suggests that the counting is stopped. A waveform of the scanning state in FIG. 4 represents the state of scanning the charged particle beam 1. The upper side (state 1) of the scanning state suggests that the charged particle beam 1 is stopped at an irradiation spot, and the lower side (state 0) of the scanning state suggests that the charged particle beam 1 is traveling to the next irradiation spot. Even when the scanning of the charged particle beam 1 to the next irradiation spot has been started, the spot counter 13 continues the measurement until the spot delay time T1 elapses. The spot delay time T1 corresponds to a control delay before control of the X-direction scanning electromagnet 2 and the Y-direction scanning electromagnet 3 for the scanning to the next irradiation spot is started.

When receiving from the scanning electromagnet power source 7 a command setting completion signal corresponding to the next spot identity SID ("0002" in FIG. 4) that has been transmitted to the X-direction scanning electromagnet 2 and the Y-direction scanning electromagnet 3 at the time instant t3, the irradiation control apparatus 10 transmits to the integrated control unit 40 of the beam position monitor 30 the inter-spot travel completion signal siga indicating that setting of a command, corresponding to the next spot identity SID ("0002" in FIG. 4), to the X-direction scanning electromagnet 2 and the Y-direction scanning electromagnet 3 has been completed.

When receiving the inter-spot travel completion signal siga, the integrated control unit 40 implements the spot initial data collection command procedure. When receiving the processing start signal sigcm, the A/D converter 33 in each of the X data processing unit 16m and the Y data processing unit 17m implements the spot initial data collection procedure.

When a predetermined time (start delay time) equivalent to the difference between the respective rise times of the processing start signal sigcm and the processing start signal sigcs elapses from the time instant t5, i.e., at the time instant t6, the integrated control unit 40 implements spot intermediate data collection command procedure. When receiving the processing start signal sigcs from the integrated control unit 40, the A/D converter 33 in each of the X data processing unit 16s and the Y data processing unit 17s implements the spot intermediate data collection procedure. The dose of the charged particle beam 1 is in the state of dose completion reaching the desired irradiation dose at an irradiation spot corresponding to the spot identity SID; when receiving the dose completion signal from the trigger generation unit 12 of the dose data converter 6, the irradiation control apparatus 10 transmits a command corresponding to the next spot identity STD to the X-direction scanning electromagnet 2 and the Y-direction scanning electromagnet 3 and concurrently outputs the dose completion signal sigb to the integrated control unit 40 (the time instant t7 in FIG. 4).

The A/D converter 33 in each of the channel data conversion units 21a through 21n implements the AD conversion processing for the spot ID ("0002 in FIG. 4), which has been commanded by the spot initial data collection command procedure at the time instant t5; after the completion of the AD conversion processing, the A/D converter 33 transmits beam data to the position size processing unit 23. Based on the beam data collected in the channel data conversion units 21a through 21n, the position size processing unit 23 calculates the beam position P and the beam size S (the position size calculation procedure).

After receiving the beam position P and the beam size S from the position size processing unit 23, the abnormality determination processing unit 24 determines whether or not the beam position P and the beam size S are allowable, based on the preset data PD. For example, when determining, with regard to the result of the second calculation in Measurement 1, that the beam position P is not allowable, the abnormality determination processing unit 24 outputs the position abnormality signal sige1 to the irradiation control apparatus 10 (the time instant t8 in FIG. 4). The irradiation control apparatus 10 receives the position abnormality signal sige1 and then cancels the beam-on command sigs2 after an interlock operation time T3 has elapsed. In this situation, cancellation of the beam-on command sigs2 is equivalent to issuing a command of turning off the beam. In response to the cancellation of the beam-on signal sigs2, the beam generation apparatus 52 stops the generation of the charged particle beam 1.

The operation of the position size processing unit 23 will be explained by use of a flowchart. FIG. 5 is a flowchart for explaining the operation of the position size processing unit. In the step ST01, the position size processing unit 23 receives the spot identity SID. In the step ST02, the position size processing unit 23 receives a voltage Vi, which has been AD-converted, from the channel data conversion unit 21. In the step ST03, the respective voltages Vi are converted into predetermined proportions wi. The proportion wi corresponds to the weight utilized when the beam position P is calculated in such a manner as a gravity center is calculated.

In the step ST04, the position size processing unit 23 calculates, through the equations (1) and (2) below, the beam position P (Px, Py) in such a manner as a gravity is calculated. The position size processing unit 23 of the X data processing unit 16 calculates the beam position Px; the position size processing unit 23 of the Y data processing unit 17 calculates the beam position Py.

$$Px = \Sigma(wix \times Xi)/\Sigma wix \quad (1)$$

$$Py = \Sigma(wiy \times Yi)/\Sigma wiy \quad (2)$$

where Xi is the X coordinate of "i" in the X channel of the position monitor 4, and Yi is the Y coordinate of "i" in the Y channel of the position monitor 4; wix is the proportion obtained converting the voltage Vi of "i" in the X channel, and wiy is the proportion obtained converting the voltage Vi of "i" in the Y channel.

In the step ST04, after completion of the calculation of the beam position P (Px, Py), the position size processing unit transmits the calculated beam position P (Px, Py) to the abnormality determination processing unit 24. In the step ST05, the position size processing unit 23 stores the beam position P (Px, Py) in the data memory 25 in such a way that the beam position P (Px, Py) corresponds to the spot identity SID. The position data that corresponds to the position monitor 4a, which is the primary position monitor, is P (Pxm, Pym); the position data that corresponds to the position monitor 4b, which is the secondary position monitor, is P (Pxs, Pys).

In the step ST06, the position size processing unit 23 calculates, through the equations (3) and (4) below, the beam size S (Sx, Sy) in such a manner as a standard deviation is calculated.

$$Sx = \mathrm{sqr}(\Sigma wix \times (Xi-Px)^2 / \Sigma wix) \quad (3)$$

$$Sy = \mathrm{sqr}(\Sigma wiy \times (Yi-Py)^2 / \Sigma wiy) \quad (4)$$

where sqr is a function for performing a root calculation, and n is the sum of calculation subjects in the X and Y channels.

In the step ST06, after completion of the calculation of the beam size S (Sx, Sy), the position size processing unit 23 transmits the calculated beam size S (Sx, Sy) to the abnormality determination processing unit 24. In the step ST07, the position size processing unit 23 stores the beam size S (Sx, Sy) in the data memory 25 in such a way that the beam size S (Sx, Sy) corresponds to the spot identity SID. The beam size that corresponds to the position monitor 4a, which is the primary position monitor, is S (Sxm, Sym); the beam size that corresponds to the position monitor 4b, which is the secondary position monitor, is S (Sxs, Sys).

The operation of the abnormality determination processing unit 24 will be explained by use of a flowchart. FIG. 6 is a flowchart for explaining the operation of the abnormality determination processing unit. In the step ST11, the abnormality determination processing unit 24 receives the spot identity SID. In the step ST12, the abnormality determination processing unit obtains the position allowable value AP and the size allowable value AS corresponding to the spot identity SID from the preset data PD. In the step ST13, the abnormality determination processing unit 24 receives the beam position P (Px, Py) from the position size processing unit 23. The respective abnormality determination processing units 24 in the X data processing unit 16m, the X data processing unit 16s, Y data processing unit 17m, and the Y data processing unit 17s receive the beam positions Pxm, Pxs, Pym, and Pys from the respective position size processing units 23, respectively.

In the step ST14, the abnormality determination processing unit 24 determines whether or not there exists a positional abnormality. In other words, the abnormality determination processing unit 24 determines whether or not the absolute value of the difference ΔP (ΔPx, ΔPy) between the beam position P (Px, Py) and the desired position Pd (Pdx, Pdy) is larger than the position allowable value AP. In the case where the absolute value of the difference ΔP is larger than the position allowable value AP, the abnormality determination processing unit 24 transmits the position abnormality signal sige1 to the irradiation control apparatus 10. The abnormality determination processing unit 24 of the X data processing unit 16m performs determination on the data for which it is responsible and then transmits the position abnormality signal sige1xm to the irradiation control apparatus 10; the abnormality determination processing unit 24 of the Y data processing unit 17m performs determination on the data for which it is responsible and then transmits the position abnormality signal sige1ym to the irradiation control apparatus 10. Similarly, the abnormality determination processing unit 24 of the X data processing unit 16s performs determination on the data for which it is responsible and then transmits the position abnormality signal sige1xs to the irradiation control apparatus 10; the abnormality determination processing unit 24 of the Y data processing unit 17s performs determination on the data for which it is responsible and then transmits the position abnormality signal sige1ys to the irradiation control apparatus 10.

In the step ST15, the abnormality determination processing unit 24 receives the beam size S (Sx, Sy) from the position size processing unit 23. In the step ST16, the abnormality determination processing unit 24 determines whether or not there exists a beam size abnormality. In other words, the abnormality determination processing unit 24 determines whether or not the absolute value of the difference ΔS (ΔSx, ΔSy) between the beam size S (Sx, Sy) and the desired beam size Sd (Sdx, Sdy) is larger than the size allowable value AS. In the case where the absolute value of the difference ΔS is larger than the size allowable value AS, the abnormality determination processing unit 24 transmits the size abnormality signal sige2 to the irradiation control apparatus 10. The abnormality determination processing unit 24 of the X data processing unit 16m performs determination on the data for which it is responsible and then transmits the size abnormality signal sige2xm to the irradiation control apparatus 10; the abnormality determination processing unit 24 of the Y data processing unit 17m performs determination on the data for which it is responsible and then transmits the size abnormality signal sige2ym to the irradiation control apparatus 10. Similarly, the abnormality determination processing unit 24 of the X data processing unit 16s performs determination on the data for which it is responsible and then transmits the size abnormality signal sige2xs to the irradiation control apparatus 10; the abnormality determination processing unit 24 of the Y data processing unit 17s performs determination on the data for which it is responsible and then transmits the size abnormality signal sige2ys to the irradiation control apparatus 10.

In the step ST17, in the case where it is determined that there exists a positional abnormality or a beam size abnormality, the abnormality determination processing unit 24 stores information indicating that there exists a positional abnormality or a beam size abnormality in the data memory 25 in such a way that the information corresponds to the spot identity SID.

Even in the case where radiations caused when the charged particle beam 1 is irradiated provide an effect, the beam position monitor 30 according to Embodiment 1 can obtain the irradiation position P and the beam size S of the charged particle beam 1 in a short obtaining cycle, unlike a conventional beam position monitor. Even in the case where the irradiation position data obtaining cycle is shorter than the irradiation position data processing time, the beam position monitor 30 can continue obtaining the irradiation position data at the scanning-stop irradiation point. The beam position monitor 30 can obtain the irradiation position P and the beam size S of the charged particle beam 1 in a short obtaining cycle; therefore, unlike a conventional beam position monitor, by obtaining data twice or more times at a single and the same scanning-stop irradiation point or by shortening the irradiation time at an irradiation spot, the time for a single therapy in the particle-beam therapy can be shortened.

The beam position monitor 30 according to Embodiment 1 can twice or more times detect the irradiation position P and the beam size S of the charged particle beam 1 while the charged particle beam 1 is stopped at an irradiation spot; therefore, each time the irradiation position P and the beam size S of the charged particle beam 1 are detected, the beam data processing device 11 can determine whether or not there exists a positional abnormality or a size abnormality in the charged particle beam 1. Accordingly, the beam position monitor 30 twice or more times detects the irradiation position P and the beam size S of the charged particle beam 1 while the charged particle beam 1 is stopped at an irradiation spot, and determines whether or not there exists a positional abnormality or a size abnormality in the charged particle beam 1 each time the irradiation position P and the beam size S of the charged particle beam 1 are detected; therefore, even in the case where when the charged particle beam 1 is stopped at an irradiation spot and is being irradiated, a positional abnormality or a size abnormality is caused in the charged particle beam 1, an abnormality detection signal indicating that there exists a positional abnormality or a size abnormality in the charged particle beam 1 can be generated.

When a positional abnormality or a size abnormality is caused in the charged particle beam 1, the beam position monitor 30 according to Embodiment 1 transmits the position abnormality signal sige1 (sige1xm, sige1xs, sige1ym, sige1ys) indicating a positional abnormality or the size abnormality signal sige2 (sige1xm, sige2xs, sige2ym, sige2ys) indicating a size abnormality to the irradiation control apparatus 10 in the irradiation management apparatus 8. In the case where while the charged particle beam 1 is irradiated, a positional abnormality or a size abnormality in the charged particle beam 1 is caused, the irradiation control apparatus 10 receives the position abnormality signal sige1 or the size abnormality signal sige2 from the beam position monitor 30, so that interlock processing, which is emergency stop processing, can be implemented.

The beam position monitor 30 according to Embodiment 1 is configured in such a way as to include a plurality of position monitors 4a and 4b, the data processing unit 22 that processes current signals from the position monitors 4a and 4b, and the integrated control unit 40 and in such a way that the current signals from the plurality of position monitors 4a and 4b are alternately processed, i.e., in such a way that, as represented in Measurements 1 and 2 in FIG. 4, even when the channel data conversion units 21a through 21n for one position monitor are processing data, the channel data conversion units 21a through 21n for the other position monitor process data; therefore, even in the case where a single AD conversion processing takes a long time, data collection and AD conversion processing at a single irradiation spot can be implemented twice or more times. The beam position monitor 30 alternately processes the current signals from the plurality of position monitors 4a and 4b; therefore, because it is not required to make a particle-beam therapy treatment plan restricted by the processing time of the A/D converter 33, there can be made a treatment plan in which a single therapy irradiation is completed in a shorter time. In other words, the therapy time can be shortened.

The particle beam irradiation apparatus 58 according to Embodiment 1 is provided with the beam position monitor 30; therefore, even in the case where radiations caused when the charged particle beam 1 is irradiated provide an effect, the particle beam irradiation apparatus 58 can obtain the irradiation position P and the beam size S of the charged particle beam 1 in a short obtaining cycle. Even in the case where the irradiation position data obtaining cycle is shorter than the irradiation position data processing time, the particle beam irradiation apparatus 58 can continue obtaining the irradiation position data at the scanning-stop irradiation point. The particle beam irradiation apparatus 58 can obtain the irradiation position P and the beam size s of the charged particle beam 1 in a short obtaining cycle; therefore, by obtaining data twice or more times at a single and the same scanning-stop irradiation point, high-accuracy and safety-raised charged particle beam irradiation can be implemented, or by shortening the irradiation time at an irradiation spot, the time for a single therapy in the particle-beam therapy can be shortened.

Because being provided with the beam position monitor 30, the particle beam irradiation apparatus 58 according to Embodiment 1 can twice or more times detect the irradiation position P and the beam size S of the charged particle beam 1 while the charged particle beam 1 is stopped at an irradiation spot; therefore, each time the irradiation position P and the beam size S of the charged particle beam 1 are detected, the particle beam irradiation apparatus 58 can determine whether or not there exists a positional abnormality or a size abnormality in the charged particle beam 1. Accordingly, the particle beam irradiation apparatus 58 twice or more times detects the irradiation position P and the beam size S of the charged particle beam 1 while the charged particle beam 1 is stopped at an irradiation spot, and determines whether or not there exists a positional abnormality or a size abnormality in the charged particle beam 1 each time the irradiation position P and the beam size S of the charged particle beam 1 are detected; therefore, even in the case where when the charged particle beam 1 is stopped at an irradiation spot and is being irradiated, a positional abnormality or a size abnormality is caused in the charged particle beam 1, an abnormality detection signal Indicating that there exists a positional abnormality or a size abnormality in the charged particle beam 1 can be generated.

The particle beam irradiation apparatus 58 according to Embodiment 1 is provided with the beam position monitor 30; therefore, in the case where while the charged particle beam 1 is irradiated, a positional abnormality or a size abnormality in the charged particle beam 1 is caused, the irradiation control apparatus 58 receives the position abnormality signal sige1 or the size abnormality signal sige2 from the beam position monitor 30, so that interlock processing, which is emergency stop processing, can be implemented. Accordingly, in the case where a positional abnormality or a size abnormality is caused in the charged particle beam 1, the particle beam irradiation apparatus 58 can stop the irradiation of the charged particle beam 1 in a short time.

The particle beam therapy system 51 according to Embodiment 1 is provided with the beam position monitor 30; therefore, even in the case where radiations caused when the charged particle beam 1 is irradiated provide an effect, the particle beam therapy system 51 can obtain the irradiation position P and the beam size S of the charged particle beam 1 in a short obtaining cycle. Even in the case where the irradiation position data obtaining cycle is shorter than the irradiation position data processing time, the particle beam therapy system 51 can continue obtaining the irradiation position data at the scanning-stop irradiation point. The particle beam therapy system 51 can obtain the irradiation position P and the beam size s of the charged particle beam 1 in a short obtaining cycle; therefore, by obtaining data twice or more times at a single and the same scanning-stop irradiation point, high-accuracy and safety-raised charged particle beam irradiation can be implemented, or by shortening the irradiation time at an irradiation spot, the time for a single therapy in the particle-beam therapy can be shortened.

Because being provided with the beam position monitor 30, the particle beam therapy system 51 according to Embodiment 1 can twice or more times detect the irradiation position P and the beam size S of the charged particle beam 1 while the charged particle beam 1 is stopped at an irradiation spot; therefore, each time the irradiation position P and the beam size S of the charged particle beam 1 are detected, the particle beam therapy system 51 can determine whether or not there exists a positional abnormality or a size abnormality in the charged particle beam 1. Accordingly, the particle beam therapy system 51 twice or more times detects the irradiation position P and the beam size S of the charged particle beam 1 while the charged particle beam 1 is stopped at an irradiation spot, and determines whether or not there exists a positional abnormality or a size abnormality in the charged particle beam 1 each time the irradiation position P and the beam size S of the charged particle beam 1 are detected; therefore, even in the case where when the charged particle beam 1 is stopped at an irradiation spot and is being irradiated, a positional abnormality or a size abnormality is caused in the charged particle beam 1, an abnormality detection signal indicating that there exists a positional abnormality or a size abnormality in the charged particle beam 1 can be generated.

The particle beam therapy system 51 according to Embodiment 1 is provided with the beam position monitor 30; therefore, in the case where while the charged particle beam 1 is irradiated, a positional abnormality or a size abnormality in the charged particle beam 1 is caused, the particle beam therapy system 51 receives the position abnormality signal sige1 or the size abnormality signal sige2 from the beam data processing device 11, so that interlock processing, which is emergency stop processing, can be implemented. Accordingly, in the case where a positional abnormality or a size abnormality is caused in the charged particle beam 1, the particle beam therapy system 51 can stop the irradiation of the charged particle beam 1 in a short time.

As described above, the beam position monitor 30 according to Embodiment 1 is provided with a plurality of position monitors 4 that detect the passing position of the charged particle beam 1 through a plurality of detection channels and the beam data processing device 11 that performs calculation processing of the state of the charged particle beam 1, based on a plurality of analogue signals outputted from the plurality of position monitors 4; the beam data processing device 11 includes a plurality of channel data conversion units 21 that perform AD conversion processing in which each of the plurality of analogue signals outputted from the position monitors 4 is converted into a digital signal, the position size processing unit 23, for each position monitor 4, that calculates the beam position P, which is the passing position of the charged particle beam 1 in the position monitor 4, based on a plurality of voltage information items obtained through processing by the plurality of channel data conversion units 21, and the integrated control unit 40 that controls the plurality of channel data conversion units 21 in such a way that while the charges particle beam 1 is irradiated onto the irradiation subject 15, AD conversion processing is performed at different timings for the respective position monitors 4. As a result, by making the integrated control unit 40 control the plurality of channel data conversion units 21 in such a way that the plurality of analogue signals are AD-converted at different timings for the respective corresponding position monitors 4, the irradiation position P of the charged particle beam 1 can be obtained in a short obtaining cycle even in the case where radiations, emitted when the charged particle beam 1 is irradiated, provide an effect.

The particle beam therapy system 51 according to Embodiment is provided with the beam generation apparatus 52 that generates the charged particle beam 1 and accelerates it by means of the accelerator 54, the beam transport system 59 that transports the charged particle beam 1 accelerated by the accelerator 54, and the particle beam irradiation apparatus 58 that irradiates the charged particle beam 1 transported by the beam transport system 59 onto the irradiation subject 15. The particle beam irradiation apparatus 58 includes the scanning electromagnets 2 and 3 that scan the charged particle beam 1 to be irradiated onto the irradiation subject 15 and the beam position monitor 30 that applies calculation processing to the state of the charged particle beam 1 that has been scanned by the scanning electromagnets 2 and 3. In the particle beam therapy system 51 according to Embodiment 1, the beam position monitor 30 of the particle beam irradiation apparatus 58 is provided with a plurality of position monitors 4 that detect the passing position of the charged particle beam 1 through a plurality of detection channels; and the beam data processing device 11 that performs calculation processing of the state of the charged particle beam 1, based on a plurality of analogue signals outputted from the plurality of position monitors 4. The beam data processing device 11 includes a plurality of channel data conversion units 21 that perform AD conversion processing in which each of the plurality of analogue signals outputted from the position monitors 4 is converted into a digital signal, the position size processing unit 23, for each of the position monitors 4, that calculates the beam position P, which is the passing position of the charged particle beam 1 in the position monitor 4, based on a plurality of voltage information items obtained through processing by the plurality of channel data conversion units 21, and the integrated control unit 40 that controls the plurality of channel data conversion units 21 in such a way that while the charges particle beam 1 is irradiated onto the irradiation subject 15, AD conversion processing is performed at different timings for the respective position monitors 4. As a result, by making the integrated control unit 40 control the plurality of channel data conversion units 21 in such a way that the plurality of analogue signals are AD-converted at different timings for the respective corresponding position monitors 4, the irradiation position P or the beam size S of the charged particle beam 1 can be obtained in a short obtaining cycle even in the case where radiations, emitted when the charged particle beam 1 is irradiated, provide an effect; thus, in the particle-beam therapy, the irradiation position P can frequently be obtained.

With regard to the position allowable value AP and the size allowable value AS, there has been explained an example in which for the primary position monitor 4a and the secondary position monitor 4b, different allowable values are utilized; however, in the case where it can be assumed that in the primary position monitor 4a and the secondary position monitor 4b, the charged particle beam 1 is a parallel beam, a single and the same allowable value may be utilized for the primary position monitor 4a and the secondary position monitor 4b. There has been explained a case where there exist two position monitors 4; however, there may be three position monitors. In the case where there exist two position monitors 4, there is a merit that the size of the beam position monitor 30 can be minimized. In the case where two position monitors 4 are utilized, the two position monitors 4 can effectively be utilized, when it is obligated to provide at least two position monitors 4.

The operation of the beam position monitor 30 has been explained with an example in which data on the charged particle beam 1 is collected twice while the charged particle beam 1 is stopped; however, it may be allowed that while he charged particle beam 1 is stopped, the data is collected many times. In a general particle beam therapy, the irradiation time at a time when the charged particle beam is stopped is longer than the spot traveling time. Even in this case, by alternately processing the current signals from the position monitors 4a and 4b, it is made possible that in an irradiation spot, data items such as the irradiation position P and the beam size S of the charged particle beam 1 can be obtained twice or more times.

In the case where the cycle of the processing start signal sigcm for commanding the start of processing of the position monitor 4a and the cycle of the processing start signal sigcs for commanding the start of processing of the position monitor 4b are set in the following manner, the treatment plan can readily be created even when data is collected many times while the charge particle beam is stopped; therefore, because a great number of possible treatment plans can be created, an optimum treatment plan can readily be determined. For example, based on the AD conversion processing time of the AD converter 33, the basic cycle is set in such a way that the AD conversion processing times of the same AD converters 33 do not overlap with one another but can be lined up in a timing chart.

The difference ΔP (ΔPx, ΔPy) between the beam position P (Px, Py) and the desired position Pd (Pdx, Pdy), which is calculated by the abnormality determination processing unit 24, can be transmitted, as position feedback information, to the irradiation control apparatus 10. The irradiation control apparatus 10 may control the position of the charged particle beam 1, based on the position feedback information. Through the foregoing method, a positional deviation, which is not large enough to be determined as a positional abnormality, can be corrected.

In the flowchart in FIG. 5, an example has been explained in which the beam position P is calculated and then the beam size S is calculated; however, it may be allowed that two calculation units perform parallel processing of the beam position P and the beam size S. In this case, in the flowchart in FIG. 6, it may be allowed that data, out of the beam position P and the beam size S, that arrives earlier than the other is determined (position abnormality determination or size abnormality determination).

DESCRIPTION OF REFERENCE NUMERALS

1: charged particle beam
2: X-direction scanning electromagnet
3: Y-direction scanning electromagnet
4, 4a, 4b: position monitor
11: beam data processing device
15: irradiation subject
21, 21a, 21n: channel data conversion unit
23: position size processing unit
24: abnormality determination processing unit
30: beam position monitor
40: integrated control unit
51: particle beam therapy system
52: beam generation apparatus
54: synchrotron
58, 58a, 58b: particle beam irradiation apparatus
59: beam transport system
P, Px, Py, Pxm, Pym, Pxs, Pys: beam position
Pd, Pdx, Pdy, Pdxm, Pdym, Pdxs, Pdys: desired position
AP, APm, APs: position allowable value
S, Sx, Sy, Sxm, Sym, Sxs, Sys: beam size
Sd, Sdx, Sdy, Sdxm, Sdym, Sdxs, Sdys: desired beam size
AS, ASm, ASs: size allowable value
siga: inter-spot travel completion signal
sigb: dose completion signal
sigcm, sigcs: processing start signal
Sige1, sige1$xm$, sige1$xs$, sige1$ym$, sige1$ys$: position abnormality signal
sige2, sige2$xm$, sige2$xs$, sige2$ym$, sige2$ys$: size abnormality signal

The invention claimed is:

1. A beam position monitor that performs calculation processing of the state of a charged particle beam that has been accelerated by an accelerator and scanned by a scanning electromagnet, the beam position monitor comprising:
a plurality of position monitors that detect a passing position of the charged particle beam through a plurality of detection channels; and
a beam data processing device that performs calculation processing of the state of the charged particle beam, based on a plurality of analogue signals outputted from the plurality of position monitors, wherein the beam data processing device includes a plurality of channel data conversion units that perform AD conversion processing in which each of the plurality of analogue signals outputted from the position monitors is converted into a digital signal; a position size processing unit, for each of the position monitors, that calculates a beam position, which is a passing position of the charged particle beam in the position monitor, based on a plurality of voltage information items obtained through processing by the plurality of channel data conversion units; and an integrated control unit that controls the plurality of channel data conversion units in such a way that while the charges particle beam is irradiated onto an irradiation subject, the AD conversion processing is performed at different timings for the respective position monitors.

2. The beam position monitor according to claim 1, wherein each time receiving an inter-spot travel completion signal indicating that setting of a command to the scanning electromagnet that scans the charged particle beam on a desired position has been completed, the integrated control unit outputs a processing start signal for starting the AD conversion processing to a data conversion unit group, among a plurality of data conversion unit groups established by grouping the channel data conversion units for the respective position monitors, that has not implemented the AD conversion processing; then, when a predetermined start delay time elapses after the processing start signal has been outputted, the integrated control unit outputs a processing start signal for starting the AD conversion processing to another data conversion unit group that has not implemented the AD conversion processing.

3. The beam position monitor according to claim 1, wherein the beam data processing device includes an abnormality determination processing unit, for each of the position monitors, that determines, based on a desired position of the charged particle beam and a position allowable value of the charged particle beam, whether or not the beam position calculated by the position size processing unit is within a tolerance range and that generates a position abnormality signal when determining that the beam position is not within the tolerance range.

4. The beam position monitor according to claim 3, wherein the number of the provided position monitors is two; and the integrated control unit outputs the processing start signal for starting the AD conversion processing alternately to two of the data conversion groups.

5. The beam position monitor according to claim 3, wherein the position size processing unit calculates a beam size of the charged particle beam that passes through the position monitor, based on the plurality of voltage information items obtained through processing by the plurality of channel data conversion units; and wherein the abnormality determination processing unit determines, based on a desired beam size of the charged particle beam and a size allowable value of the charged particle beam, whether or not the beam size is within a tolerance range and that generates a size abnormality signal when determining that the beam size is not within the tolerance range.

6. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject,
wherein the particle beam irradiation apparatus includes a scanning electromagnet that scans a charged particle beam to be irradiated onto the irradiation subject and a beam position monitor that applies calculation processing to the state of the charged particle beam that has been scanned by the scanning electromagnet; and
wherein the beam position monitor is the beam position monitor according to claim 1.

7. The beam position monitor according to claim 2, wherein the beam data processing device includes an abnormality determination processing unit, for each of the position monitors, that determines, based on a desired position of the charged particle beam and a position allowable value of the charged particle beam, whether or not the beam position calculated by the position size processing unit is within a tolerance range and that generates a position abnormality signal when determining that the beam position is not within the tolerance range.

8. The beam position monitor according to claim 2, wherein the number of the provided position monitors is two; and the integrated control unit outputs the processing start signal for starting the AD conversion processing alternately to two of the data conversion groups.

9. The beam position monitor according to claim 7, wherein the number of the provided position monitors is two; and the integrated control unit outputs the processing start signal for starting the AD conversion processing alternately to two of the data conversion groups.

10. The beam position monitor according to claim 4,
wherein the position size processing unit calculates a beam size of the charged particle beam that passes through the position monitor, based on the plurality of voltage information items obtained through processing by the plurality of channel data conversion units; and
wherein the abnormality determination processing unit determines, based on a desired beam size of the charged particle beam and a size allowable value of the charged particle beam, whether or not the beam size is within a tolerance range and that generates a size abnormality signal when determining that the beam size is not within the tolerance range.

11. The beam position monitor according to claim 7,
wherein the position size processing unit calculates a beam size of the charged particle beam that passes through the position monitor, based on the plurality of voltage information items obtained through processing by the plurality of channel data conversion units; and
wherein the abnormality determination processing unit determines, based on a desired beam size of the charged particle beam and a size allowable value of the charged particle beam, whether or not the beam size is within a tolerance range and that generates a size abnormality signal when determining that the beam size is not within the tolerance range.

12. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject,
wherein the particle beam irradiation apparatus includes a scanning electromagnet that scans a charged particle beam to be irradiated onto the irradiation subject and a beam position monitor that applies calculation processing to the state of the charged particle beam that has been scanned by the scanning electromagnet; and
wherein the beam position monitor is the beam position monitor according to claim 2.

13. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject,
wherein the particle beam irradiation apparatus includes a scanning electromagnet that scans a charged particle beam to be irradiated onto the irradiation subject and a beam position monitor that applies calculation processing to the state of the charged particle beam that has been scanned by the scanning electromagnet; and
wherein the beam position monitor is the beam position monitor according to claim 3.

14. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject,
wherein the particle beam irradiation apparatus includes a scanning electromagnet that scans a charged particle beam to be irradiated onto the irradiation subject and a beam position monitor that applies calculation processing to the state of the charged particle beam that has been scanned by the scanning electromagnet; and
wherein the beam position monitor is the beam position monitor according to claim 4.

15. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject,
wherein the particle beam irradiation apparatus includes a scanning electromagnet that scans a charged particle beam to be irradiated onto the irradiation subject and a beam position monitor that applies calculation processing to the state of the charged particle beam that has been scanned by the scanning electromagnet; and
    wherein the beam position monitor is the beam position monitor according to claim 5.

16. A particle beam therapy system comprising:
   a beam generation apparatus that generates a charged particle beam and accelerates the charged particle beam by means of an accelerator;
   a beam transport system that transports the charged particle beam accelerated by the accelerator; and
   a particle beam irradiation apparatus that irradiates the charged particle beam transported by the beam transport system onto an irradiation subject,
   wherein the particle beam irradiation apparatus includes
a scanning electromagnet that scans a charged particle beam to be irradiated onto the irradiation subject and a beam position monitor that applies calculation processing to the state of the charged particle beam that has been scanned by the scanning electromagnet; and
    wherein the beam position monitor is the beam position monitor according to claim 7.

17. A particle beam therapy system comprising:
   a beam generation apparatus that generates a charged particle beam and accelerates the charged particle beam by means of an accelerator;
   a beam transport system that transports the charged particle beam accelerated by the accelerator; and
   a particle beam irradiation apparatus that irradiates the charged particle beam transported by the beam transport system onto an irradiation subject,
   wherein the particle beam irradiation apparatus includes
a scanning electromagnet that scans a charged particle beam to be irradiated onto the irradiation subject and a beam position monitor that applies calculation processing to the state of the charged particle beam that has been scanned by the scanning electromagnet; and
    wherein the beam position monitor is the beam position monitor according to claim 8.

18. A particle beam therapy system comprising:
   a beam generation apparatus that generates a charged particle beam and accelerates the charged particle beam by means of an accelerator;
   a beam transport system that transports the charged particle beam accelerated by the accelerator; and
   a particle beam irradiation apparatus that irradiates the charged particle beam transported by the beam transport system onto an irradiation subject,
   wherein the particle beam irradiation apparatus includes a scanning electromagnet that scans a charged particle beam to be irradiated onto the irradiation subject and a beam position monitor that applies calculation processing to the state of the charged particle beam that has been scanned by the scanning electromagnet; and
   wherein the beam position monitor is the beam position monitor according to claim 10.

* * * * *